(12) United States Patent
Orange et al.

(10) Patent No.: US 6,560,946 B2
(45) Date of Patent: May 13, 2003

(54) AUTOMATIC DISTRIBUTOR FOR CONTAINER COVERS

(75) Inventors: Christian Orange, Bricquebec (FR); Philippe Hunaut, Greville-Hague (FR)

(73) Assignee: Campagnie Generale des Matieres Nucleaires, Velizy Villacoublay (FR)

( * ) Notice: Subject to any disclaimer, the term of this patent is extended or adjusted under 35 U.S.C. 154(b) by 0 days.

(21) Appl. No.: 09/882,864

(22) Filed: Jun. 15, 2001

(65) Prior Publication Data

US 2001/0052483 A1 Dec. 20, 2001

(30) Foreign Application Priority Data

Jun. 16, 2000 (FR) .............................. 00 07715

(51) Int. Cl.⁷ .............................. B65B 7/28; B67B 3/06
(52) U.S. Cl. .............................. 53/310; 53/311; 221/222
(58) Field of Search ........................ 53/306, 310, 311; 221/222, 231

(56) References Cited

U.S. PATENT DOCUMENTS

| | | | | |
|---|---|---|---|---|
| 2,015,913 A | * | 10/1935 | Von Sydow et al. | 221/293 |
| 2,264,738 A | * | 12/1941 | Blann | 221/238 |
| 2,840,963 A | * | 7/1958 | Osmond | 221/222 |
| 2,841,939 A | * | 7/1958 | Marceau | 221/187 |
| 3,426,941 A | * | 2/1969 | Hovekamp | 101/35 |
| 3,712,483 A | * | 1/1973 | Messervey | 221/222 |
| 3,741,410 A | * | 6/1973 | Henschke et al. | 221/222 |
| 3,755,987 A | | 9/1973 | Dardaine et al. | |
| 3,894,379 A | | 7/1975 | Naggert | |
| 4,257,532 A | | 3/1981 | Amberg | |
| 5,020,297 A | | 6/1991 | Borie et al. | |

* cited by examiner

*Primary Examiner*—M. D. Patterson
(74) *Attorney, Agent, or Firm*—Pearne & Gordon LLP

(57) ABSTRACT

The present invention relates to a distributor that enables covers to be fitted automatically on containers in a chamber without requiring assistance from an operator. It mainly comprises a slider (5) mounted to slide between two plates (3 and 4). The queued covers (2D) are positioned on a lowering and introducing system (11) equipped with three double-fingers (20) that enable the last bottom cover to be selected in each cycle in order for it to drop onto the slider (5). A carrier cell (7) in said slider is used to displace the selected cover towards a positioning cell (9) of the lower plate (4) and drop it onto a container that has been previously introduced by said cell.

4 Claims, 4 Drawing Sheets

AUTOMATIC DISTRIBUTOR FOR CONTAINER COVERS

FIELD OF THE INVENTION

The present invention relates to packing or packaging of products in containers that has to be performed in a special atmosphere, i.e. in a confined atmosphere, such as in glove boxes.

There are many industrial applications of this type of device and they concern, in particular, toxic or radioactive products or products that must be processed in an ultraclean atmosphere.

BACKGROUND ART AND PROBLEM POSED

Figure 1:
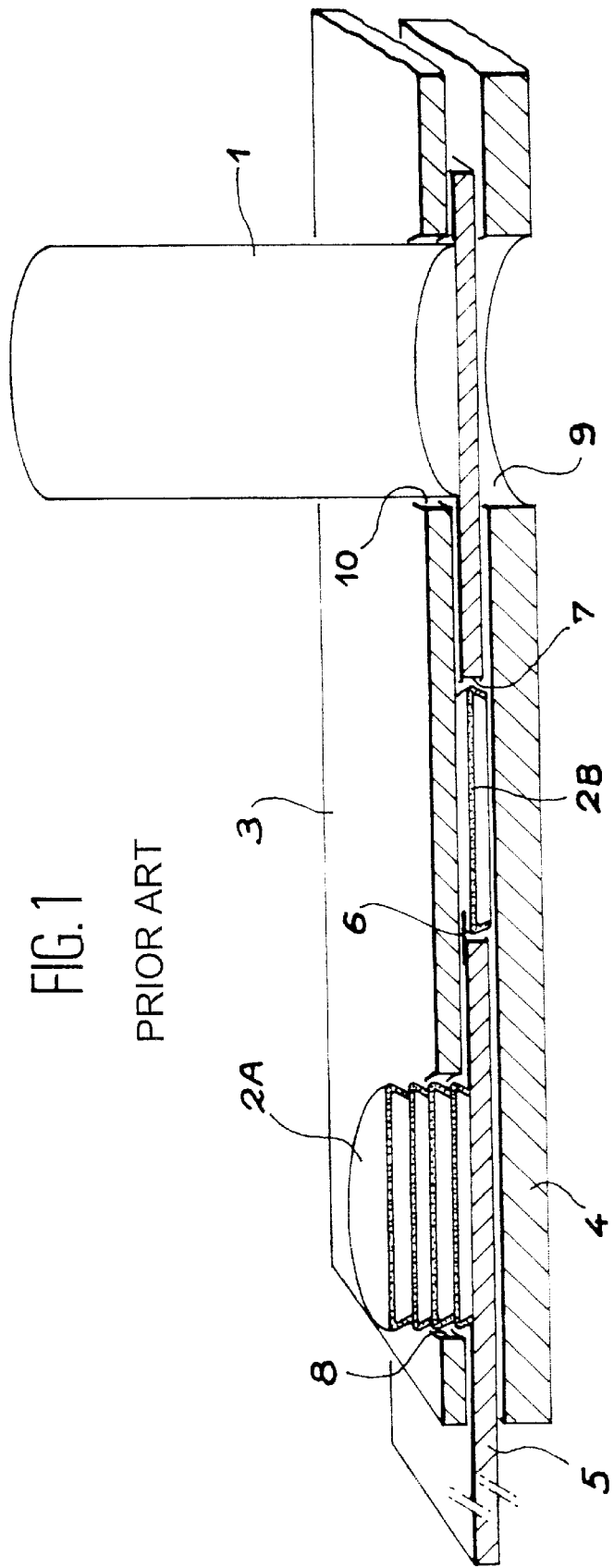

Referring to FIG. 1, one of the standard devices for distributing covers on drums in a glove box or similar chamber comprises the following main parts: a frame consisting of an upper plate 3 and a lower plate 4 parallel to one another and close together such that they provide a flat space in which a slider 5 may slide horizontally. Upper plate 3 comprises a cover positioning cell 8 the diameter of which is greater than the diameter of covers 2A to be installed on the containers and a container positioning cell 10 the diameter of which is greater than the diameter of containers 1 on which the covers are to be installed. Lower plate 4 comprises a positioning cell 9 located just under container positioning cell 10, i.e. along the same vertical axis.

Slider 5 is also equipped with a cover carrier cell 7 for carrying covers 2A located in cover positioning cell 8 one by one towards positioning cell 9. A gripping tab 6 is positioned horizontally on slider 5 and projects inside carrier cell 7 on the upper surface of slider 5. Therefore, when slider 5 is withdrawn to the left and carrier cell 7 is positioned under the pile of covers 2A, the cover at the bottom of said pile drops into carrier cell 7. As slider 5 is slightly thicker than each cover 2A gripping tab 6 enables only lower cover 2B to be removed from the pile of covers 2A, preventing the following cover from being also removed or bent. It should be noted that this operation is facilitated by the slightly sloping lateral shape of the covers to be handled.

When slider 5 is withdrawn into the position for gripping cover 2B to be carried it does not obstruct the container positioning cell 10 or positioning cell 9. Consequently, container 1, which is previously positioned in container positioning cell 10, passes through the distributor and is positioned on a device that transfers it towards a filling point. When the slider is pushed towards the right it takes with it a carried cover 2B to positioning cell 9 in which said cover falls onto the upper section of the container positioned on the transfer device.

Nevertheless, this type of device presents problems in as far as reliability is concerned, mainly due to the covers repeatedly becoming jammed when they are carried horizontally and to poor feed of the covers. The aim of the present invention is to overcome these drawbacks by using a slider distributor that operates reliably and that does not require human handling.

SUMMARY OF THE INVENTION

To this end, the invention mainly relates to a container cover distributor comprising:
a frame composed mainly of:
   an upper plate comprising two cells, one of which is used to position the containers and the other of which is used to position the covers in a pile; and
   a lower plate comprising a cell for positioning the containers and covers in a determined space located in the same axis under the cell into which the containers from the upper plate are introduced; and
   a flat slider mounted to slide between the upper and lower plates comprising a carrier cell to receive and displace a cover taken from the bottom of the pile towards the container and cover positioning cell.

According to the invention, the distributor comprises a device for automatically lowering and introducing covers one by one into the carrier cell of the slider.

In the preferred embodiment of the distributor the device for lowering and introducing the cover comprises:
at least three double-fingers spread around the cover positioning cell to maintain the pile of covers just above the slider and to separate the bottom cover of the pile and free it to drop it into the carrier cell, said three double-fingers being mounted to pivot on the upper plate;
a ring for actuating the double-fingers, mounted to rotate around the positioning cell of the covers of the upper plate.

In the preferred embodiment of the ring, said ring has the same number of housings as double-fingers in each of which a stud is positioned that is connected to each of the double-fingers and that causes alternate successive rotations of said double-fingers when said ring revolves. In the preferred embodiment of the double-fingers each one comprises:
a gripping finger in a low position that uses the lower cover to maintain the pile of covers above the slider; and
a separating finger in a high position, one end of which is knife-shaped to separate the two lower covers, the space between the two fingers being greater than the thickness of one of the covers, the two fingers being offset at an angle to each other.

In the preferred embodiment of the distributor a device is used to set the ring rotating that comprises:
a pusher connected to the slider to push the ring into rotation; and
a pin that projects radially relative to the ring and against which the pusher comes to bear.

A return device is also preferably used that comprises:
a rod mounted to slide horizontally relative to the upper plate;
a return spring around the rod that is compressed by the rod and that comes to bear on a fixed stop of the upper plate; and
a fixed stop on the upper plate to halt the rotating movement of the ring when the slider is withdrawn.

List of Figures

Figure 2:
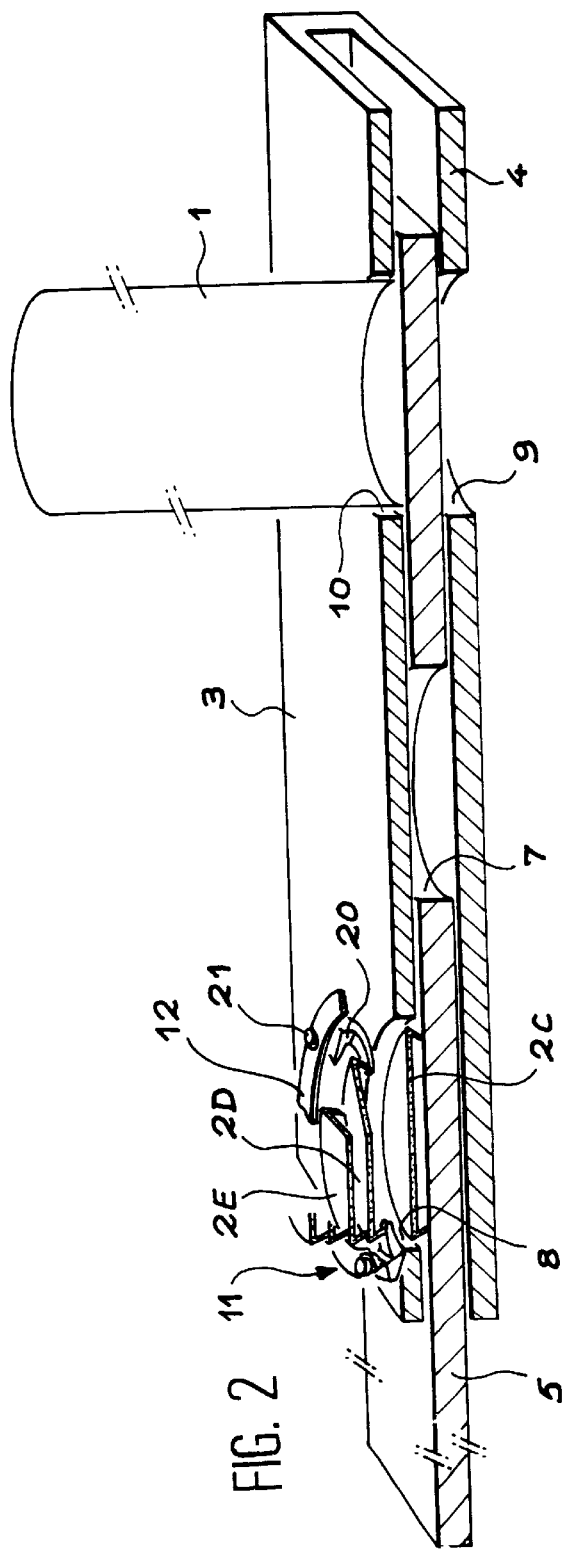
Figure 3:
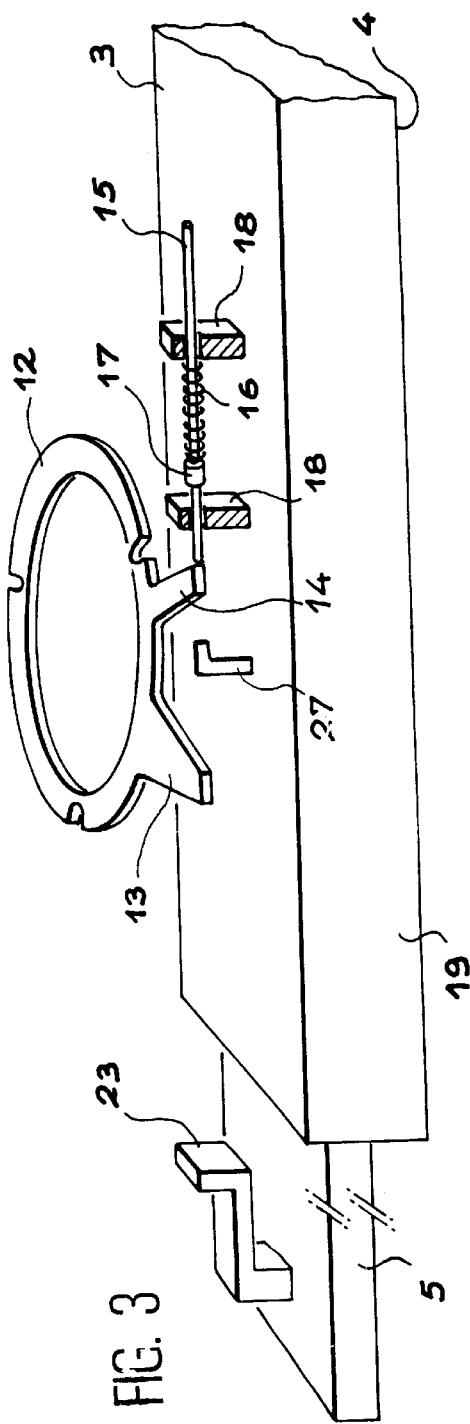
Figure 4:
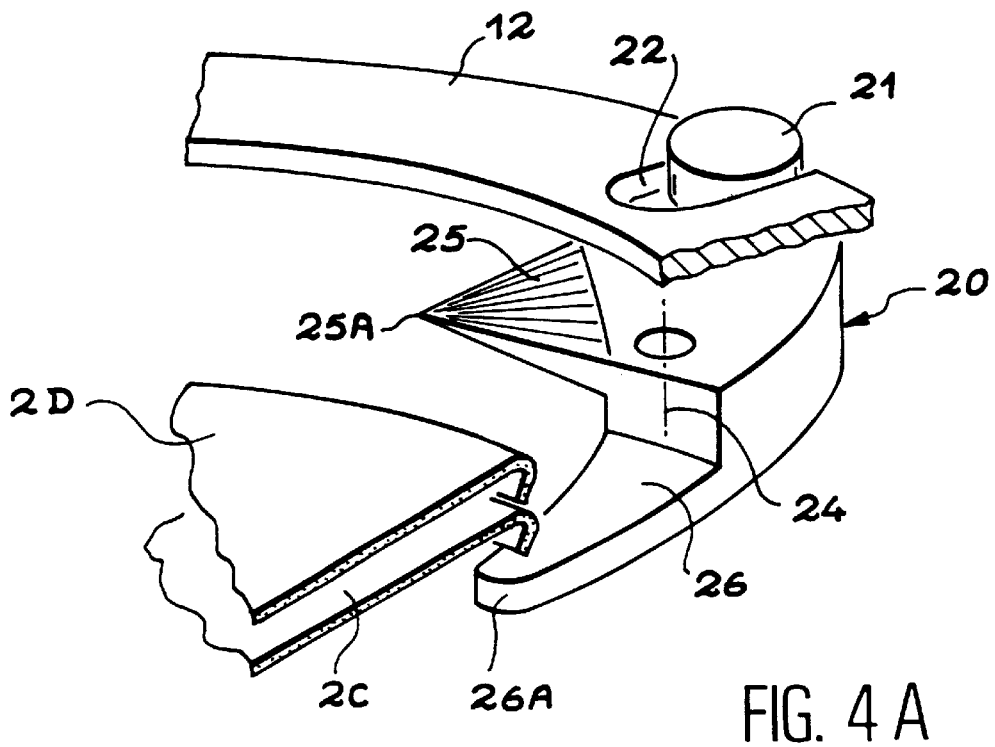
Figure 4:
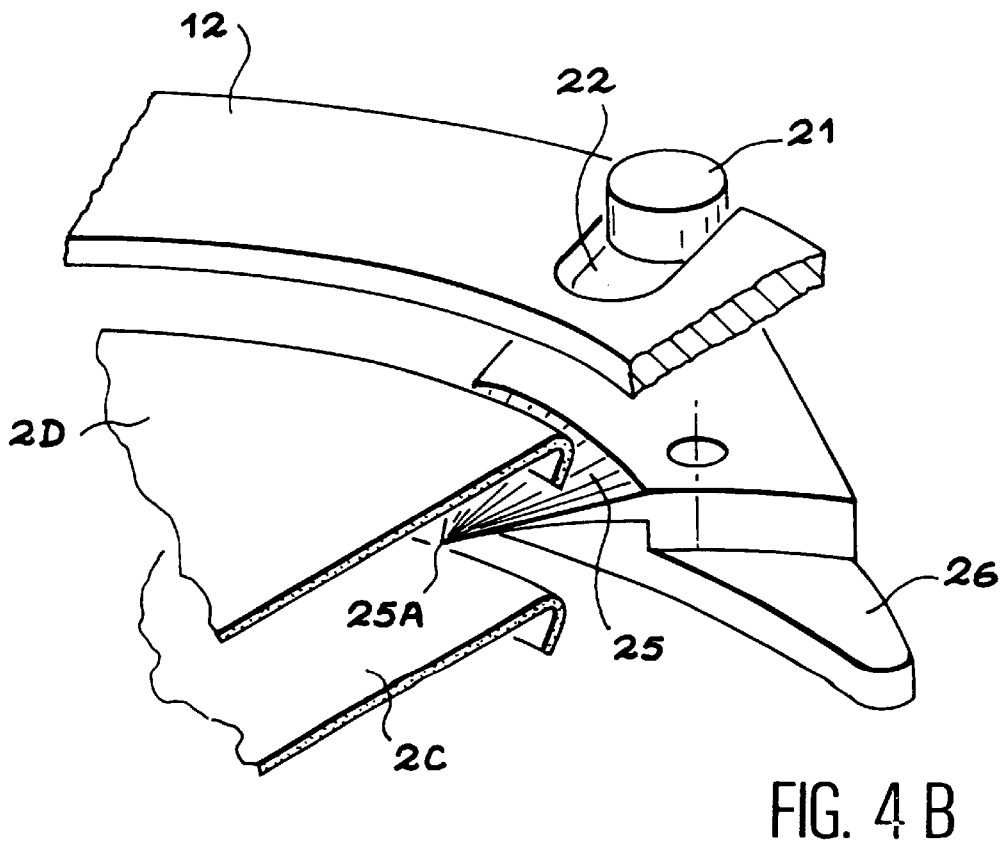
Figure 5A:
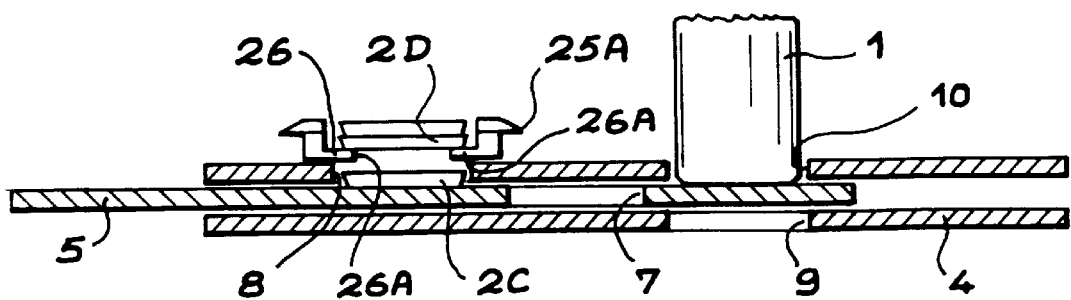
Figure 5B:
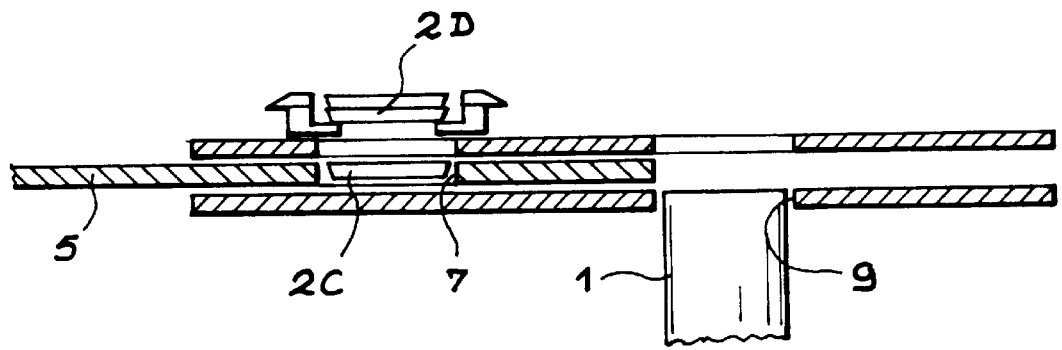
Figure 5C:
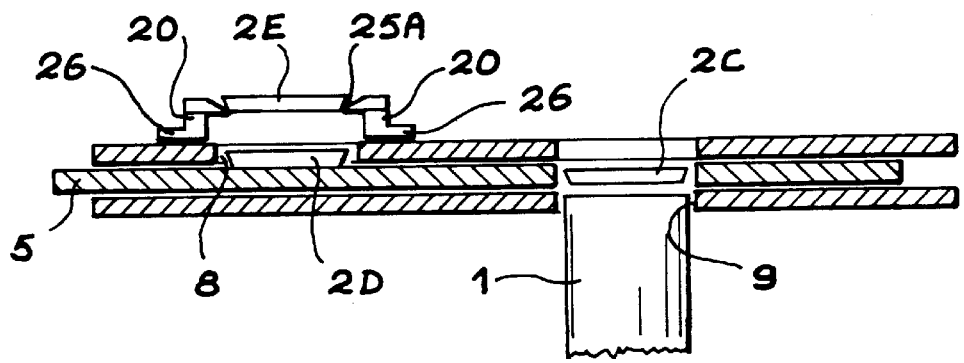

The invention and its various technical characteristics will be better understood from the following description and several figures wherein:
FIG. 1 (described above) is a distributor of the prior art;
FIG. 2 is a cross-section of the distributor of the invention;
FIG. 3 is a detail of a section of the distributor of the invention;
FIGS. 4A and 4B are details of an embodiment of the device for lowering and introducing covers into the carrier cell of the slider; and
FIGS. 5A, 5B and 5C are cross-sections showing the three main operating phases of the device of the invention.

DETAILED DESCRIPTION OF AN EMBODIMENT OF THE INVENTION

Referring to FIG. 2, the distributor of the invention comprises the same main parts of the prior art, namely an upper plate 3 and a lower plate 4 between which the carrier slider 5 slides. These three parts include the same cells as those of the distributor of the prior art, namely two distribution cells for upper plate 3: one (reference 8) for covers 2A positioned in a pile and the other (reference 10) for containers 1. Lower plate 4 still comprises positioning cell 9 located just under container positioning cell 10. Slider 5 also comprises the same carrier cell 7.

The main characteristic of the invention is that the distributor comprises an automatic device 11 for lowering and introducing covers 2A, which are positioned in a pile, in cover positioning cell 8. The device mainly comprises a ring 12 consisting of a flat ring mounted to rotate around the vertical axis of cover positioning cell 8. Ring 12 is wider than cover positioning cell 8 and has three housings each of which contains a stud 21 connected to a double-finger 20 that is mounted to pivot on an upper plate 3. Each double-finger 20 comprises two fingers used, on the one hand, to hold the pile of covers 2A in place by inserting itself under the lower cover of the pile of covers 2A and, on the other, by separating said lower cover from the rest of the pile of covers 2A. Ring 12 is used to pivot double-fingers 20 such that one or other of the fingers is actuated alternately. The mechanism that drives ring 12 to rotate is shown in FIG. 3 while FIGS. 4A and 4B show the operation of the two fingers of double-finger 20.

In FIG. 3 the frame of the distributor is shown as a casing mainly consisting of upper plate 3 and lower plate 4 that are fastened relative to each other by lateral surfaces 19. Slider 5, which is mounted inside, includes a pusher 23 intended to push a control pin 13 to rotate ring 12 and that projects radially relative to said ring. Ring 12 includes a second pin that is a return pin 14 that also projects radially and that comes to bear on a rod 15 mounted to slide relative to upper plate 3.

The positioning and sliding of rod 15 are ensured by two feet 18 in which it is mounted to slide. The movement of rod 15 is controlled by return pin 14 pushing rod 15 towards the right. Said rod is equipped with a return spring 16 and a stopped ring 17, which forms an integral part of said rod, both parts being located between the two feet 18 that support rod 15. When ring 12 rotates under the effect of pusher 23, which bears on control pin 13, spring 16 is compressed by stopped ring 17. When slider 5 is brought back to its initial position return spring 16 pushes back rod 15 that pushes return pin 14 causing ring 12 to rotate in the opposite direction. Contact is maintained between pusher 23 and control pin 13 when slider 5 is first withdrawn causing the rotating ring 12 to brake. The rotation movement is stopped when return pin 14 comes into contact with a fixed stop 27 connected to upper plate 3. Slider 5 continues its withdrawal movement, pusher 23 moves away from control pin 13 and ring 12 remains immobile, return spring 16 ensuring residual pressure on rod 15 that forces return pin 14 up against stop 27. When pusher 23 pushes control arm 13 and return spring 16 is compressed, carrier cell 7 of slider 5 is aligned with container positioning cell 10 and positioning cell 9 (see FIG. 2).

Referring to FIG. 4A, each double-finger 20 mainly comprises an upper finger 25 and a lower finger 26 that are offset relative to each other at an angle of approximately 120° and separated in height by a distance that is slightly greater than the thickness of each of the covers 2C and 2D of the pile of covers. It should be noted that the two upper 25 and lower fingers 26 are directed towards the inside of ring 12.

Each double-finger 20 is mounted such that it is mobile and rotates around a axis of vertical rotation 24 that lies virtually at the apex of the angle created by the two upper 25 and lower fingers 26. It may easily be understood that during the alternate successive rotations of double-finger 20 the respective ends 25A and 26A of upper 25 and lower fingers 26 penetrate alternately inside of the circle defined by the inside of ring 12. When lower finger 26 is directed inside ring 12, as shown in FIG. 4A, upper finger 25 is folded back under ring 12 and its end 25A is not therefore in the surface defined by the inside of ring 12. Consequently, end 26A of lower finger 26 is positioned under lower cover 2C of the pile of covers.

Stud 21, which is fastened to double-finger 20, is positioned in a housing 22 of ring 12. Consequently, when said ring rotates, stud 21 is driven along a circular trajectory around axis of vertical rotation 24 by housing 22 causing upper 25 and lower arm 26 to change position relative to one another.

After this type of rotation lower arm 26 is folded back under ring 12 whereas upper arm 25 projects inside said ring, as shown in FIG. 4B. End 25a of upper finger 25 is pointed or knife-blade shaped which enables it to penetrate between two successive covers and particularly between lower cover 2C and cover 2D immediately above it. Lower cover 2C is therefore separated relative to the other covers.

Three double-fingers 20, which are spaced at 120° around ring 12, are sufficient to support the pile of covers 2C and 2D. However, a larger number of double-fingers 20 may also be envisaged.

Referring to FIGS. 5A, 5B and 5C, the distributor, and particularly the lowering and introducing device, operate as follows:

In FIG. 5A, slider 5 is in the intermediary position, i.e. carrier cell 7 is between the positions of cover positioning cell 8 and container positioning cell 10. Consequently, container 1, which is ready to be positioned on the transfer device and displaced towards a filling point, is positioned on slider 5. Similarly, lower cover 2C is positioned on slider 5. On the other hand, ends 26A of lower fingers 26 support the pile of covers and particularly lower cover 2D. Removed cover 2C no longer therefore belongs to the queued covers.

In FIG. 5B slider 5 is pushed towards the left such that carrier cell 7 lies under pile of covers 2D. Consequently, cover 2C deposited on slider 5 drops into carrier cell 7. Container 1, which is queued above introduction cell 9, falls onto the device that transfers it towards the filling point via the frame consisting of upper 3 and lower plates 4.

In FIG. 5C slider 5 is pushed completely to the right. In compliance with the mechanism in FIG. 3 double-fingers 20 have pivoted around their vertical axis (not shown) Consequently, lower fingers 26 have moved away from the inside of the surface of cover positioning cell 8 and end 25A of upper fingers 25 has penetrated inside of said surface and passes under the last but one cover 2E of the pile. This configuration enables the last cover 2D to drop onto slider 5 because it is not held by upper fingers 25 of double-fingers 20.

Cover 2C, which was initially deposited on slider 5, is carried above positioning cell 9 and, consequently, above container 1 that has been positioned on the device that transfers it towards the filling point. It can therefore be positioned above said container.

Following this operation slider 5 must be pushed back towards the left to enable a new container 1 to be positioned on slider 5.

It should be noted that the covers shown in these figures have a slightly sloping rim, i.e. with the lower section that slopes slightly inwards, to enable the covers to be subsequently crimped onto the filled containers.

It will therefore easily be understood that the distributor of the invention enables covers to be distributed onto containers automatically inside a glove box without any human handling whatsoever being required.

What is claimed is:

1. Distributor for container covers comprising:
    a frame comprising:
        an upper plate comprising two cells, one of which is used to position the containers and the other is used to position the covers in a pile; and
        a lower plate comprising a cell for positioning the containers and covers in a determined space located in the same axis under the cell in to which the containers from the upper plate are introduced; and
    a flat slider mounted to slide between the upper and lower plates comprising a carrier cell to receive and displace a cover taken from the bottom of the pile towards the container and cover positioning cell,
    characterized in that said distributor comprises a device for lowering and introducing covers in a pile, the covers being dropped one by one into said carrier cell of the slider, the device for lowering and introducing the covers comprising:
        at least three double fingers placed around the cover positioning cell to maintain the pile of covers just above the slider and separate the bottom cover of the pile and free it to drop it into the carrier cell, said three double-fingers being mounted to pivot on the upper plate,
        a ring having the same number of housings as double-fingers in each of which a stud is positioned that is connected to each of the double-fingers and that causes alternate successive rotations of said double-fingers when said ring revolves;
        a device used to set the ring rotating comprising:
            a pusher connected to the slider to push the ring; and
            a control pin that projects radially relative to the ring and against which the pusher comes to bear.

2. Distributor of claim 1 characterized in that each of the double-fingers comprises:
    an upper finger intended to separate covers positioned at an upper level and one end of which is knife-shaped to separate two lower covers; and
    a lower finger located at a lower level that uses the bottom cover to maintain the pile of covers,
    a space between the two upper and lower fingers being greater than a thickness of one of the covers, the two fingers being offset at an angle to each other.

3. Distributor for container covers comprising:
    a frame comprising:
        an upper plate comprising two cells, one of which is used to position the containers and the other is used to position the covers in a pile; and
        a lower plate comprising a cell for positioning the containers and covers in a determined space located in the same axis under the cell in to which the containers from the upper plate are introduced; and
    a flat slider mounted to slide between the upper and lower plates comprising a carrier cell to receive and displace a cover taken from the bottom of the pile towards the container and cover positioning cell,
    characterized in that said distributor comprises a device for lowering and introducing covers in a pile, the covers being dropped one by one into said carrier cell of the slider, at least three double fingers placed around the cover positioning cell to maintain the pile of covers just above the slider and separate the bottom cover of the pile and free it to drop it into the carrier cell, said three double-fingers being mounted to pivot on the upper plate,
    a ring having the same number of housings as double-fingers in each of which a stud is positioned that is connected to each of the double-fingers and that causes alternate successive rotations of said double-fingers when the ring revolves,
    further characterized in that said distributor comprises a device for returning the ring to its initial position consisting of:
        a rod mounted to slide horizontally relative to the upper plate;
        a return spring fitted around the rod that comes to bear on a fixed foot of the upper plate and that is compressed by a stopped ring connected to said rod; and
        a fixed stop to stop the rotating movement of the ring when the slider is withdrawn.

4. Distributor for container covers comprising:
    a frame comprising an upper plate comprising a first cell for positioning containers and a second cell for positioning covers in a pile, and a lower plate comprising a cell for positioning the containers and the covers in a determined space located under said first cell of said upper plate;
    a slider mounted to slide between the upper plate and the lower plate, said slider comprising a carrier cell to receive and displace a cover taken from the bottom of the pile towards the cell of said lower plate; and
    a device for lowering and introducing the covers in a pile comprising:
        at least three finger elements placed around the cover positioning cell, each of said finger elements comprising: an upper finger which extends transversely relative to a rotational axis of said finger member and includes a pointed peripheral edge, a lower finger disposed below said upper finger and extending transversely relative to the rotational axis, said upper finger and said lower finger being offset at an angle to each other, and a stud that extends upwardly from said finger element;
        a ring having openings, each of which receives one of said studs, and
        means for rotating said ring in either direction, wherein said rotation of said ring engages said studs enabling said finger elements to rotate such that the upper fingers can alternately separate covers of the pile and not engage the covers in said pile and said lower fingers can alternately maintain the pile of covers above said slider and drop a separated lower cover into said carrier cell.

* * * * *